United States Patent
Moore et al.

[11] Patent Number: 5,866,825
[45] Date of Patent: Feb. 2, 1999

[54] RINSING TRAY FOR MULTIPIPETTING DEVICE

[75] Inventors: Thomas Moore; Uwe Naumann, both of Jena, Germany

[73] Assignee: OPALJENA Gesellschaft fuer optische Analytik und Labortechnik mbH, Jena, Germany

[21] Appl. No.: 911,903

[22] Filed: Aug. 15, 1997

[30] Foreign Application Priority Data

Aug. 30, 1996 [DE] Germany .................. 196 35 004.2

[51] Int. Cl.$^6$ ............................................. G01N 21/00
[52] U.S. Cl. .............................. 73/864.22; 422/99
[58] Field of Search ....................... 73/863, 863.32, 73/864.17, 864.22; 422/99; 134/166 R, 170, 166 C, 22.11, 23, 84, 85, 88, 91

[56] References Cited

U.S. PATENT DOCUMENTS

| Re. 30,562 | 3/1981 | Park | 422/99 |
| 3,649,464 | 3/1972 | Freeman | 422/99 |
| 4,554,839 | 11/1985 | Hewett et al. | |
| 5,182,082 | 1/1993 | Monthony et al. | 422/58 |

FOREIGN PATENT DOCUMENTS

| 37 12 776 | 10/1987 | Germany . |
| 3712776 | 10/1987 | Germany . |
| 43 14 180 | 11/1993 | Germany . |

OTHER PUBLICATIONS

Patent Abstracts of Japan, P–962, Nov. 20, 1989, vol. 13/No. 517, #1–209371 / Aug. 23, 1989, Hitachi Ltd. "Cleaner".
Patent Abstracts of Japan, P–962, Nov. 20, 1989, vol. 13/No. 517, #1–209372 / Aug. 23, 1989, Toshiba Corp. "Cleaner for Automatic Chemical Analyzer".
Patent Abstracts of Japan, Publication No. 07–103986 / Apr. 21, 1995, Kayagaki Irika Kogyo KK, "Method of Cleaning Nozzle for Inspection and Dilution/Dispersion Device for Inspection".

*Primary Examiner*—Robert Raevis
*Attorney, Agent, or Firm*—McAulay Nissen Goldberg Kiel & Hand, LLP

[57] ABSTRACT

A rinsing tray system for cleaning the pipette tips of a multipipetting device is described. The rinsing tray system substantially comprises a first tray and a second tray below the latter, these two trays communicating via openings which are arranged in the same grid dimension as the pipette tips of a multipipetting device. The openings are made in webs so that the rinsing liquid located in the first tray can flow into the second tray only by means of the pipette tips and not directly. The rinsing tray system according to the invention enables a particularly time-saving and space-saving cleaning of the pipette tips of a multipipetting device.

9 Claims, 2 Drawing Sheets

RINSING TRAY FOR MULTIPIPETTING DEVICE

BACKGROUND OF THE INVENTION a) Field of the Invention

The invention is directed to a rinsing tray system for cleaning the pipette tips of a multipipetting device.

b) Description of the Related Art

A feature common to all multipipetting devices is that they simultaneously take up liquids into the pipette tips from supply vessels so that these liquids can then be emptied into one or more vessels again, namely, Terasiki plates or microtitration plates, as they are called.

These multipipetting devices mostly operate on the principle of air displacement. That is, e.g., 96 pistons (arranged in an 8×12 grid pattern) are moved by a common driving means and generate a vacuum or overpressure in 96 air spaces formed by the piston seal and the pipette tip, so that liquids can be taken up or emptied into the microtitration plates.

The microtitration plates have depressions or wells for receiving liquids, wherein the wells are arranged in an 8×12 grid pattern and generally have a distance from center to center of 9 mm.

There are basically two ways of handling microtitration plates. Either the microtitration plate is brought to the pipette tips of the multipipetting device by means of a lifter or the pipette ties along with the entire pipetting arrangement are brought to the microtitration plate.

In a number of cases of application, it is desirable not to exchange the pipette tips of the multipipetting device, but rather to wash them out and clean them with a rinsing agent. Often, this is done by taking up liquid into the pipette tip from a refillable vessel and then emptying it out again into another drop vessel, as it is called. This process is usually repeated several times. The rinsing or cleaning is time-consuming principally because the appropriate vessel must be brought over and then brought back again, and the drop vessel must then be brought over and brought back again. This requires not only a minimum transporting distance corresponding to the dimensions of the vessels, but also necessitates additional space in the device.

OBJECT AND SUMMARY OF THE INVENTION

The primary object of the invention is to provide a rinsing tray system for a multipipetting device of the type mentioned above which makes it possible to rinse the pipette tips of a multipipetting device in the most time-saving and space-saving manner possible.

This object is met, according to the invention, by a rinsing tray system for a multipipetting device having pipette tips arranged in matrix-form and containing a first tray for receiving the unused rinsing liquid and a second tray for receiving the used rinsing liquid in that the first tray is arranged so as to be seated on top of the second tray, in that there are openings on the bottom of the first tray in the same grid dimension as the matrix-shaped pipette tip arrangement, in that there are raised webs (i.e., hollow cylinders) around the openings so that the unused rinsing liquid can only flow out of the first tray when the filling level is higher than the webs, and in that the webs are so dimensioned that the pipette tips of the multipipetting device which are arranged in a matrix shape can be lowered, with respect to the openings for emptying the used rinsing liquid through these openings into the second tray, in at least one direction, offset preferably by an amount corresponding to half the grid dimension, for receiving the unused rinsing liquid up to, at most, the bottom of the first tray.

In order to remove the used rinsing liquid from the second tray as quickly as possible, it has proven advantageous to provide an outlet at the deepest or lowest point so that the rinsing liquid can run off through the outlet by gravitational force or be sucked out through the outlet.

The first tray advantageously has an inlet for filling and draining. It is further advantageous when the first tray has an overflow, so that when filling with unused rinsing liquid this unused rinsing liquid does not flow off via the opening into the second tray. Alternatively, it is equally conceivable to install a filling level sensor instead of the overflow such that when the maximum (web height) or desired filling level is reached the supply of unused rinsing liquid is shut off. In order for the rinsing liquid to be distributed throughout the first tray as rapidly as possible, this distributing process can be accelerated, assuming that the webs are arranged in rows, in that the webs are combined in groups of two with respect to the openings. It also is possible for every web to have only one opening into the second tray. In a particularly advantageous manner, every web has two openings. In this way, particularly simple techniques can be used to make a vent opening between the two openings so that suction of the used rinsing liquid out of the second tray can be dispensed with in favor of a flowing off due to gravitational force since the exit of air from the second tray is ensured via the vent openings.

In the interest of neatness, it is useful and advantageous to provide the first tray with a cover, wherein the cover must have through-holes corresponding to the pipette tips arranged in matrix shape for receiving the unused rinsing liquid and must further have through-holes over the openings of the webs, preferably so as to be offset by half the grid dimension, for emptying the received rinsing liquid into the second tray.

The invention will be explained more fully hereinafter with reference to an embodiment example.

DESCRIPTION OF THE PREFERRED EMBODIMENTS

Figure 1:
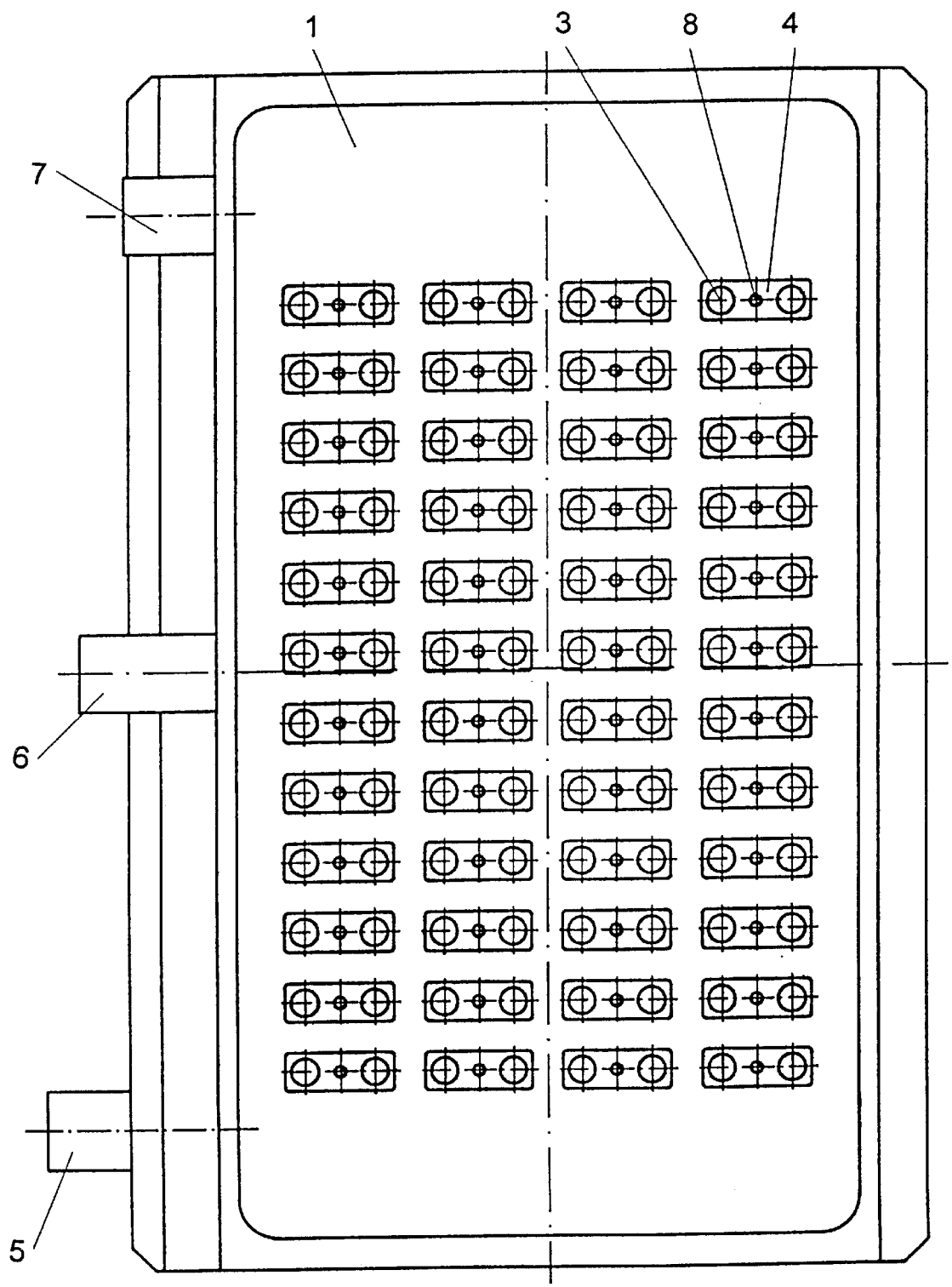
FIG. 1 shows a top view of a rinsing tray system according to the invention.

The basic construction of the rinsing tray system according to the invention comprises a first tray 1 and a second tray 2 situated below the latter. Webs 4 (i.e., hollow cylinders) can be clearly discerned in FIG. 1. Each web 4 has two openings 3 and a vent opening 8 therebetween. FIG. 1 further shows the outlet 5, the inlet 6 and the overflow 7. The openings 3 which are arranged in a matrix shape, as is shown in FIG. 1, correspond exactly to the grid dimension of the pipette tips of a multipipetting device.

Figure 2:
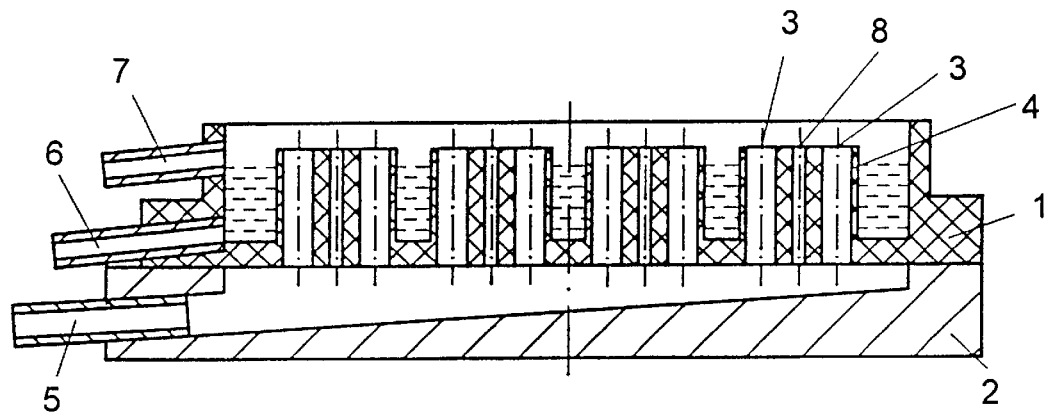
FIG. 2 shows a section through the rinsing tray system shown in FIG. 1.

The first tray 1 is first filled with rinsing liquid via the inlet 6. It is clear from FIG. 2 that the rinsing liquid cannot reach the height of the webs 4 because the overflow 7 comes into play before this and the rinsing liquid is accordingly prevented from flowing off into the second tray 2 via the openings 3. It would also be readily possible to replace the overflow 7 with a filling level sensor, not shown, in order to regulate the influx of rinsing liquid. When there is a sufficient amount of rinsing liquid in the first tray 1, either the rinsing tray system is brought to the pipette tips or vice versa, depending on the actual construction of the multipipetting device. In accordance with the configuration of the webs 4 selected in FIG. 1, the rinsing tray system is brought to all of the pipette tips of the multipipetting device in such a way that immersion in the first tray 1 is made possible for taking up the rinsing liquid contained therein. In this instance, the pipette tips are positionally offset from the positions of the openings 3 (such offset corresponding to half a so-called grid dimension and such offset being either above or below the opening.

After taking up the rinsing liquid into the pipette tips, the rest of the rinsing liquid can be changed via the inlet 6 in the first tray 1, since the remaining rinsing liquid could have become contaminated also by the immersion of the pipette tips.

After the pipette tips are lowered and released, the rinsing tray system can be displaced over the webs 4 by half the grid dimension vertically to the lowering direction (down or up with respect to the drawing according to FIG. 1). As a result of this displacement, all of the pipette tips of the multipipetting device are now located over the openings 3. The rinsing liquid can now flow from the pipette tips through the openings 3 into the second tray 2, wherein it has proven advisable to lift the rinsing tray system beforehand. The vent openings 8 ensure that the air located in the second tray 2 can escape so that there can be an undisturbed flow into the second tray 2. The vent openings 8 in the webs 4 can also be dispensed with. However, in that case, suction must be provided for via the outlet 5 so that the air located in the second tray 2 does not have a hindering effect.

After the pipette tips are emptied, rinsing can be carried out again in that the rinsing tray system need only be offset in reverse by half a grid dimension and the pipette tips can already take up new unused rinsing liquid. If the vent openings 8 are dispensed with entirely, which is another possibility that was described above, the number of webs 4 can be doubled, as can easily be seen from FIG. 1, wherein every web 4 then has only one opening 3. This is also definitely advantageous because the rinsing liquid can accordingly be distributed very quickly in the first tray 1. This is especially important when rinsing is carried out several times and the rinsing liquid must be completely changed every time. If there is sufficient time for filling with rinsing liquid, the webs 4 can be combined by rows (or columns) into one, so that in the present rinsing tray system according to the invention there would only be twelve webs 4, each with eight openings 3 (or 8 webs 4 with twelve openings 3).

Figure 3:
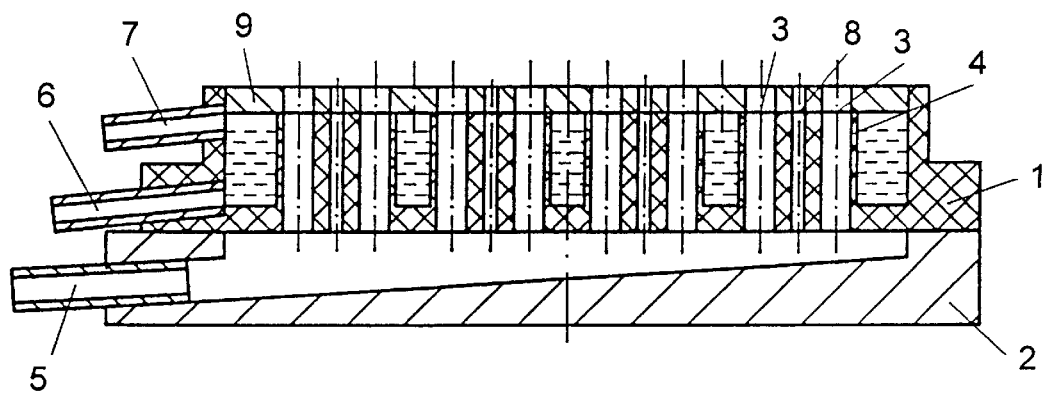
FIG. 3 shows a section through another rinsing tray system according to the invention.

In certain cases of application, it is useful to modify the rinsing tray system according to the invention as shown in FIG. 3 in such a way that the first tray 1 is provided with a cover 9. The cover 9 has through-holes exactly over the openings 3, the vent openings 8 and, in order to receive the rinsing liquid from the first tray 1, in the same grid pattern but so as to be offset by half a grid dimension with respect to the openings 3.

While the foregoing description and drawings represent the preferred embodiments of the present invention, it will be obvious to those skilled in the art that various changes and modifications may be made therein without departing from the true spirit and scope of the present invention.

What is claimed is:

1. A rinsing tray system for a multipipetting device, comprising:

a first tray for receiving unused rinsing liquid; and a second tray for receiving used rinsing liquid;

said first tray being arranged so as to be seated on top of the second tray;

said first tray having a bottom in which there are openings in a matrix form, said matrix form corresponding to a matrix form of a matrix-shaped pipette tip arrangement of the multipipetting device;

raised webs being provided around said opening of said first tray so that unused rinsing liquid is prevented from flowing out of said first tray through said openings;

said webs being so dimension that pipette tips of the multipipetting device which are arranged in a matrix shape can be lowered, with respect to the openings for emptying the used rinsing liquid through these openings into the second tray, in at least one direction, offset by an amount corresponding to half a grid dimension, for receiving the unused rinsing liquid up to, at most, the bottom of the first tray.

2. The rinsing tray system according to claim 1, wherein the second tray has an outlet at the lowest point.

3. The rinsing tray system according to claim 1, wherein the first tray has an inlet at its lowest point.

4. The rising tray system according to claim 1, wherein the first tray has an overflow which is arranged in an outer wall below the height of the web and which prevents supplied unused rinsing liquid from overflowing out of the first tray into the second tray.

5. The rinsing tray system according to claim 1, wherein the first tray contains a filling level sensor in order to prevent the supplied unused rinsing liquid from overflowing from the first tray into the second tray.

6. The rinsing tray system according to claim 1, wherein the webs are arranged in rows and every web has as many openings as the number of columns in the column arrangement of pipette tips of the multipipetting device.

7. The rinsing tray system according to claim 1, wherein each web contains two openings and the webs are aligned in rows.

8. The rinsing tray system according to claim 6, wherein vent openings are provided in the webs between adjacent openings belonging to one and the same web.

9. The rinsing tray system according to claim 1, wherein the first tray is provided with a cover, wherein the webs extend to an inner side of the cover, and said cover has through-holes therein corresponding to the grid dimension over the openings of the webs and, further, there is at least an equal quantity of through-holes in the cover, so as to be offset by half the grid dimension, for receiving unused rinsing liquid by means of the multipipetting device through these through-holes from the first tray and then letting this rinsing liquid out via the other through-holes and openings to the second tray.

* * * * *